(12) United States Patent
Hackbarth et al.

(10) Patent No.: US 9,080,976 B2
(45) Date of Patent: Jul. 14, 2015

(54) MEASURING DEVICE FOR MEASURING SINGLET OXYGEN LUMINESCENCE

(75) Inventors: Steffen Hackbarth, Berlin (DE); Jan Schlothauer, Berlin (DE)

(73) Assignee: Humbolt-Universitaet zu Berlin, Berlin (DE)

( * ) Notice: Subject to any disclaimer, the term of this patent is extended or adjusted under 35 U.S.C. 154(b) by 0 days.

(21) Appl. No.: 14/111,813

(22) PCT Filed: Apr. 12, 2012

(86) PCT No.: PCT/EP2012/056680
§ 371 (c)(1),
(2), (4) Date: Oct. 15, 2013

(87) PCT Pub. No.: WO2012/140142
PCT Pub. Date: Oct. 18, 2012

(65) Prior Publication Data
US 2014/0045272 A1    Feb. 13, 2014

(30) Foreign Application Priority Data

Apr. 15, 2011    (DE) .......................... 10 2011 007 546

(51) Int. Cl.
*G01N 21/64* (2006.01)
*G01N 21/00* (2006.01)

(52) U.S. Cl.
CPC ........ *G01N 21/6404* (2013.01); *G01N 21/6402* (2013.01); *G01N 2021/6484* (2013.01); *Y10T 436/20* (2015.01); *Y10T 436/207497* (2015.01)

(58) Field of Classification Search
CPC .......... G01N 21/6202; G01N 21/6404; G01N 21/64; G01N 21/63; G01N 21/62; G01N 21/00; Y10T 436/207497; Y10T 436/20; Y10T 436/00

USPC .......................................................... 436/136
See application file for complete search history.

(56) References Cited

U.S. PATENT DOCUMENTS 4,576,173 A    3/1986    Parker et al.
5,242,835 A    9/1993    Jensen
(Continued)

FOREIGN PATENT DOCUMENTS

AT           409 306 B      7/2002
DE         38 87 528 T2     8/1994
(Continued)

OTHER PUBLICATIONS

Jarvi et al., "The Influence of Oxygen Depletion and Photosensitizer Triplet-state Dynamics during Photodynamic Therapy on Accurate Singlet Oxygen Luminescence Monitoring and Analysis of Treatment Dose Response" Photochemistry and Photobiology, 2011, 87: 223-234.

*Primary Examiner* — Christine T Mui
(74) *Attorney, Agent, or Firm* — Laurence A. Greenberg; Werner H. Stemer; Ralph E. Locher

(57) ABSTRACT

A measuring device measures singlet oxygen luminescence which is excited by one or more photosensitizers. The measuring device contains a photosensitive detector, an excitation source, and a control and evaluating unit that is coupled to the photosensitive detector and the excitation source. The excitation source is configured to radiate excitation light into a measurement volume from a plurality of emission positions in order to excite the photosensitizer or photosensitizers. The excitation source preferably contains light-emitting diodes as lighting devices, the light of which is used directly as an excitation light in order to excite the photosensitizers.

11 Claims, 6 Drawing Sheets

(56) References Cited

U.S. PATENT DOCUMENTS

| | | |
|---|---|---|
| 5,564,419 A | 10/1996 | Lundsgaard et al. |
| 6,096,734 A | 8/2000 | Russell et al. |
| 6,143,514 A | 11/2000 | Ullman et al. |
| 6,232,130 B1 | 5/2001 | Wolf |
| 6,254,829 B1 | 7/2001 | Hartmann et al. |
| 6,555,317 B2 | 4/2003 | Lishanski et al. |
| 7,046,347 B1 | 5/2006 | Amend et al. |
| 7,229,842 B2 | 6/2007 | Singh et al. |
| 7,470,917 B1 | 12/2008 | Hoang et al. |
| 2003/0058450 A1 | 3/2003 | Mosley et al. |

FOREIGN PATENT DOCUMENTS

| | | |
|---|---|---|
| DE | 694 30 482 T2 | 11/2002 |
| DE | 692 33 146 T2 | 4/2004 |
| DE | 696 33 941 T2 | 11/2005 |
| DE | 697 36 382 T2 | 8/2007 |
| DE | 698 39 149 T2 | 2/2009 |

MEASURING DEVICE FOR MEASURING SINGLET OXYGEN LUMINESCENCE

BACKGROUND OF THE INVENTION

Field of the Invention

The invention relates to a measuring device for measuring singlet oxygen luminescence being excited by at least one photosensitizer. The measuring device includes a photosensitive detector, an excitation source, and a control and evaluation unit coupled to the photosensitive detector and the excitation source.

Molecular oxygen in nature has a so-called triplet ground state $O_2(^3S_g)$, which is designated here as triplet oxygen. In contrast thereto, most potential reaction partners in nature are present in the singlet state. On account of quantum mechanical spin selection rules, a reaction of triplet oxygen is therefore highly unlikely. By contrast, the first excited state $O_2(^1D_g)$, which is designated as singlet oxygen, is very much more reactive since here shared orbitals can be occupied. On account of the different multiplicity, it is furthermore not possible to excite an oxygen molecule from the triplet ground state to the excited singlet state by means of dipole radiation.

However, such excitation is possible in impact reactions with other molecules in an excited triplet state. The prior art discloses reaction mechanisms in which so-called photosensitizers, which are generally dye molecules, are brought to an excited state by means of excitation light being radiated in. Alongside a radiative decomposition channel of this excited state of a photosensitizer, there is a second decomposition channel, in which, by means of an intersystem crossing and an impact excitation with triplet oxygen, energy is transferred from the photosensitizer to the triplet oxygen and the latter is converted to the singlet state. The singlet oxygen is then subsequently available for reactions.

Use is made of this reaction mechanism for example in so-called photodynamic therapy, for example for combating tumors, with the use of photosensitizers that preferably accumulate in tumor cells. By means of photo-excitation, singlet oxygen can thus be generated indirectly via the photosensitizers in the tumor cells and ultimately contributes to the destruction of the tumor cells by way of its toxicity.

This is just one example of the importance of singlet oxygen in research, medicine and technology. There is great interest in studying different photosensitizers and the reaction kinetics thereof and the reaction kinetics of singlet oxygen in different chemical environments and systems. Indirect measurement methods involving the detection of reaction partners or reaction products rather than the singlet oxygen itself have often been used in the prior art.

DE 692 33 146 T2 describes, for example, particles containing a composition comprising a chemoluminescent compound, which is a substance which enters into a chemical reaction with singlet oxygen in order to form a metastable intermediate species, which can decompose with simultaneous or subsequent emission of light and a fluorescent molecule, which is excited by the activated chemoluminescent compound and emits a wavelength that is longer than the emission wavelength of the chemoluminescent compound. Furthermore, a method for detecting an analyte is described, in which a photosensitizer that is able to generate singlet oxygen is excited. The latter activates a chemoluminescent compound, the luminescence of which is evaluated.

A radiative decomposition from the excited singlet state to the triplet ground state is forbidden on account of the spin selection rules already mentioned above. Nevertheless, an, albeit very weak, luminescence of the radiation transition of singlet oxygen to the triplet oxygen ground state can be observed. The radiation of the transition has a wavelength at 1270 nm and is therefore in the near infrared wavelength range. Since only statistically about one $O_2(^1D_g)$ singlet oxygen molecule out of 2.6 million singlet oxygen molecules decomposes radiatively, it is necessary either to use a very sensitive detector or to achieve very high production rates by means of a very effective excitation of the photosensitizers.

The article by Jarvi et al. "The Influence of Oxygen Depletion and Photosensitizer Triplet-state Dynamics During Photodynamic Therapy on Accurate Singlet Oxygen Luminescence Monitoring and Analysis of Treatment Dose Response" Photochemistry and Photobiology, 2011, 87:223-234 discloses a device in which cells in a cuvette are examined when a photosensitizer is added. The cells are irradiated by means of laser radiation in the cuvette, such that the photosensitizers are excited and contribute to formation of singlet oxygen. Perpendicularly to the direction of incidence, luminescence radiation is recorded by means of a photomultiplier. The light incidence ensues in a pulsed manner and the recording of the detected luminescence photons ensues in a temporally resolved manner. The reaction dynamics can be evaluated by this means.

DE 38 87 528 T2 also describes a method for determining the oxygen content.

BRIEF SUMMARY OF THE INVENTION

The invention addresses the problem of improving known measuring devices in order in particular to provide cost-effective measurement set-ups for laboratory investigations, and of providing an improved measuring method.

The problem is solved according to the invention by means of an object as claimed in patent claim 1 and a method as claimed in claim 11. Advantageous developments of the invention are evident from the dependent claims.

The basic concept involves achieving an excitation that is as simple as possible and nevertheless very intensive in a small volume region from which the luminescence radiation can be captured on a detector. Particularly intensive incidence of radiation is achieved in a measurement volume if light is radiated into the measurement volume from different emission positions. The radiation intensity in the measurement volume can be significantly increased as a result. The incidence of radiation is effected simultaneously and jointly from the different emission positions, preferably using light having the same excitation wavelength, in order to achieve the intensive incidence of radiation in the measurement volume.

The emission position is considered to be in each case that position of an optical element or of an excitation source (light source) at which the light leaves the optical element or the light source and from which the light propagates to the excitation volume rectilinearly, disregarding light refraction at a cuvette surrounding the excitation volume.

According to the invention, an excitation source comprises at least one light emitting diode, the light from which is radiated directly as excitation light for photosensitizers into the measurement volume.

Light emitting diodes constitute very robust and reliable illuminants that are available cost-effectively for different excitation wavelengths. Since measurements for singlet oxygen luminescence are in each case temporally resolved measurements in which a pulse-like excitation of the photosensitizers takes place and the resulting luminescence is subsequently measured over a time interval, it is possible to drive the laser diodes with pulsed currents that are far above the continuous wave energization for which the light emitting diodes are designed. The luminescence efficiency can thus be increased without destroying the light emitting diodes. One important advantage of light emitting diodes over laser systems is that they can be operated without specialist personnel, are robust and do not require maintenance or complex adjustment.

One embodiment of a measuring device for measuring singlet oxygen luminescence, which is excited by means of one or a plurality of photosensitizers, comprises a photosensitive detector, an excitation source and a control and evaluation unit coupled to the photosensitive detector and the excitation source, wherein the excitation source is designed to radiate excitation light from a plurality of emission positions into a measurement volume for exciting the photosensitizer or the photosensitizers. One preferred excitation source comprises at least one light emitting diode which directly generates the light for exciting the photosensitizer or the photosensitizers in a measurement volume.

In order to achieve a high intensity in the measurement volume, it is desirable for the emission positions to be arranged as near as possible to the measurement volume.

On the other hand, it is desirable to image the largest possible proportion of the luminescence radiation that arises in the measurement volume onto the photosensitive detector. Therefore, an arrangement of the emission positions on a circle has proved to be a particularly suitable arrangement geometry.

One preferred embodiment of the invention therefore provides for at least a large number of the emission positions to be arranged on a circle, wherein the circle is arranged with respect to the measurement volume such that a midpoint of the circle is enclosed by the measurement volume or an axis oriented perpendicularly to the circle plane and running through the midpoint of the circle pierces the measurement volume.

Particularly preferably, the light exit locations, i.e. the emission positions, are arranged equidistantly on the circle. This leads to uniform illumination of the measurement volume.

A very high radiation intensity in the measurement volume can be achieved in a development in which light emitting diodes are arranged at the emission positions. Said light emitting diodes are arranged such that the maxima of the respective emission characteristic are oriented with regard to the emission intensity such that a maximum intensity is achieved in the measurement volume.

If a photosensitizer which can be excited in a specific wavelength range is used, then it is advantageous if all the light emitting diodes emit light having the same wavelength. The same applies if the intention is to make quantitative statements about the quantity of the singlet oxygen generated.

An alternative embodiment provides for optical fibers to end at the emission positions. Light for the photo-excitation can be coupled into said optical fibers at a distance from the measurement volume. In this case, light from the same illuminant can be coupled into all the optical fibers used or alternatively an illuminant can be individually assigned in each case to each optical fiber or to a group of optical fibers. Given suitable coupling of the illuminants to the optical fibers, it is possible to achieve a very good utilization of the light intensity despite the spacing apart from the measurement volume.

In order to achieve a good detection, it is desirable, as already mentioned above, to image the largest possible solid angle range of the luminescence radiation emerging from the measurement volume on the photosensitive detector. Furthermore, it is expedient to provide a measuring device that is as small and compact as possible in order to achieve this aim.

One preferred embodiment therefore provides for the measurement volume and the photosensitive detector to be aligned along a vertical axis, wherein the measurement volume is arranged above the detector, wherein an optical module is arranged between the measurement volume and the photosensitive detector, said optical module comprising an imaging optical unit, which images at least part of the luminescence radiation generated in the measurement volume onto an active area of the photosensitive detector. If the excitation is effected by means of illuminants or emission positions which are arranged on a circle, then an axis oriented through the midpoint and perpendicularly to the circle plane preferably coincides with the vertical. This enables the luminescence light to be observed transversely with respect to the excitation direction of the light. This makes it possible largely to prevent the excitation light from being imaged directly on the photosensitive detector. Furthermore, it is possible to image a luminescence radiation from a very large solid angle range on the detector. Furthermore, in the case of a perpendicular construction, the gravitational force can be utilized in order to fix individual components on components arranged underneath and, with the embodiment of suitable guides and centering devices, to center and/or fix the individual component parts and modules of the measuring device in a gravity-driven manner.

Since most examination objects are present in the liquid phase, it is necessary for the measurement volume or a region enclosing the measurement volume to be enclosed and delimited by a container. Such a container is also designated as a cuvette. In one particularly preferred embodiment, the excitation source is designed as a cuvette mount, such that a cuvette introduced into the cuvette mount remains in a gravity-driven manner in a measurement position in which a hollow volume of the cuvette encompasses the measurement volume. It is obvious to a person skilled in the art that the cuvette material must be designed to be as transparent as possible both to the wavelength of the excitation light and in particular to the wavelength of the luminescence radiation. Individual plastics materials which fulfill these requirements and exhibit a very high transmission in particular in the near infrared wavelength range are known in the prior art. Quartz glass cuvettes having a very high transmission in the near infrared wavelength range are furthermore suitable.

Particular preference is given to cuvettes which have a planar base that faces the photosensitive detector and is perpendicular to the optical axis which links the measurement volume to the photosensitive detector and at the same time constitutes the principal optical axis of the imaging optical unit. Such a planar base is preferably optically polished in order to minimize optical effects at the interface. A high surface quality is likewise desirable for a side wall of the cuvette via which the excitation is effected, but flame polishing generally suffices here.

It is desirable to detect on the photosensitive detector exclusively the radiation which can be assigned to the singlet oxygen luminescence. Therefore, it is endeavored to block light having other wavelengths or to select the luminescence light in a targeted manner. On the one hand, this could be effected by means of a so-called monochromator, but known monochromators often have an excessively poor efficiency with regard to a transmission and are furthermore complex technically and with regard to adjustment. One particularly preferred embodiment therefore comprises a bandpass filter arranged in the optical module, i.e. between the measurement volume and the photosensitive detector.

Interference filters have proved to be particularly suitable, said interference filters being formed from different layers oriented plane-parallel to one another and having different dielectric constants. For the efficacy of such an interference filter it is necessary for the light that is to be filtered to propagate only along one propagation direction, i.e. different beam propagation paths run parallel to one another. Therefore, the imaging optical unit preferably comprises at least two converging lenses between which the imaged luminescence radiation has plane-parallel beam guiding. The bandpass filter as interference filter is then arranged in this region.

In some embodiments, one of the imaging lenses is already integrated into a photosensitive detector construction. Photomultipliers, for example those such as are offered by Hamamatsu Photonics K.K. Ivatacity, Japan under the type designation H 10330-25, -45 and -75, are particularly suitable and sensitive in the range of the near infrared wavelength range.

Such a bandpass filter also protects the photosensitive detector in addition to the geometrical arrangement against the excitation light which is inevitably scattered during the intensive excitation at the photosensitizers and/or other constituents in the measurement volume.

It is obvious to a person skilled in the art that the entire measurement construction is embodied such that ambient light cannot be incident from outside either into the measurement volume or into the optical module or the detector. It therefore proves to be suitable to surround the individual modules and component parts of the measuring device with a housing, which is preferably formed from a metal, in particular from aluminum or high-grade steel, which firstly brings about a reflection of light impinging from outside, and secondly enables a good dissipation of heat that possibly arises in the interior. Both the materials mentioned are distinguished by very low interference emissions in the infrared range, which emissions would corrupt the measurement result since they take place with a very wide-band manifestation. It has been found that an emission in the infrared wavelength range that decays over time can be observed from the illuminant mount on account of the pulsed light excitation with the use of some materials. Said emission, as already mentioned above, is only very low and has a wide-band manifestation in the case of high-grade steel and aluminum. An embodiment of the individual components, in particular of the illuminant holder, made from high-grade steel or aluminum additionally brings about an effect which follows the principle of the Ulbricht sphere and which leads to a slight increase in the number of detected luminescence photons.

In order to be able to examine reaction dynamics and kinetics for different systems, it is necessary to be able to adapt an excitation wavelength of the excitation light. It has therefore proved to be particularly advantageous to configure the excitation source such that the latter comprises at least one exchangeable excitation module which can be placed onto the optical module. Particularly preferably, the excitation modules are equipped with differently configured light emitting diodes, such that each excitation module provides a different wavelength. In this case, the excitation modules can each comprise the circuits required for driving the individual light emitting diodes. However, parts of the driving electronics for the illuminants, for example light emitting diodes, said driving electronics being configured jointly for different light emitting diodes, is preferably accommodated in a driving module separate from the excitation modules. For a particularly compact construction it is advantageous if the excitation modules themselves are designed as cuvette mounts.

In order to protect the photosensitive detector against incidence of ambient light during an exchange of an excitation module, a cuvette or the like, an adjustable, fully closable iris diaphragm is preferably incorporated between the measurement volume and the photosensitive detector. Since said iris diaphragm does not have to be inserted in the beam guiding region in which the different light paths are parallelized with respect to one another, said iris diaphragm is preferably arranged at that end of the optical module which faces the measurement volume.

In order to ensure that the excitation modules can only be separated from the optical module when the iris diaphragm is closed, one preferred embodiment of the excitation modules provides for the latter to have a groove, into which an adjusting lever of the iris diaphragm engages and brings about a positively locking interlocking between the optical module and the excitation module in an open state of the iris diaphragm. When the iris diaphragm is open, separation of the excitation module from the optical module is not possible. In the closed state of the iris diaphragm, separation of the excitation module from the optical module is possible.

For some measurements it is advantageous for the substrate situated in the measurement volume to be exchanged between the individual measurement cycles. Therefore, one embodiment provides for the cuvette to comprise a tube through which a flow can take place and which encloses the measurement volume. By way of example, a tube of U-like design can be provided in the cuvette, wherein the measurement volume is preferably designed close to a base, that is to say a turning point, of the U-shaped tube.

It is obvious to a person skilled in the art that the measurement volume is principally defined by the imaging optical unit, which images the radiation of a volume region or of a solid angle range onto the detector. Preferably, the two imaging lenses have the same optical properties in order to obtain the highest possible luminous efficiency.

A simple and at the same time very reliable evaluation of a time-dependent luminescence is achieved with an evaluation circuit in which a counter is started with the triggering and/or radiating of the excitation light pulse. Said counter is used as an index counter for incremental counters that are incremented in each case when the photosensitive detector indicates the detection of a light quantum and the index counter refers to the corresponding incremental counter. The index counter thus represents a time signal. The incremental counter assigned to the corresponding index or time value is therefore incremented only when a photon is detected by the photosensitive detector at a time corresponding to the value of the index counter. Such measured value acquisition can be achieved cost-effectively by means of a field programmable gate array, which generally comprises a microcontroller, memory and logic elements in an integrated fashion in order to realize such an evaluation circuit.

Alternatively, it is also possible to use a specifically produced microchip in which such an evaluation circuit is implemented in a hardwired fashion.

The measurement results and driving with regard to a repetition frequency of the excitation light source, etc. are generally implemented by means of a computer interface, designed for example as a USB interface, RS232 interface or the like.

In order to separate for example unavoidable radiation portions which reach the photosensitive detector, but do not originate from the singlet oxygen luminescence, from said singlet oxygen luminescence, it is desirable to be able to perform a principal component analysis. For this purpose, provision is made for providing a variable bandpass filter in the optical module. In one embodiment, a tiltable interference filter is used for this purpose, which filter is connected to a stepper motor controller, for example, and can thus be varied in a targeted manner with regard to the transmission wavelength by means of tilting.

Alternatively, an adjustable interference filter with drivable liquid crystal layers can also be used. Such variable bandpass filters are sold for example by Cambridge Research & Instrumentation, Inc. (CRi) under the trade name VariSpec, for example in Europe via LOT-Oriel GmbH & Co. KG, Darmstadt, Germany.

In order to increase a yield of the detected luminescence photons of the luminescence light, one embodiment provides a measuring device that a mirror is arranged at a side of the measurement volume facing away from the detector, said mirror reflecting luminescence light into the measurement volume and/or onto the detector.

The invention is explained in greater detail below with reference to a drawing, in which:

DESCRIPTION OF THE INVENTION

Figure 1:
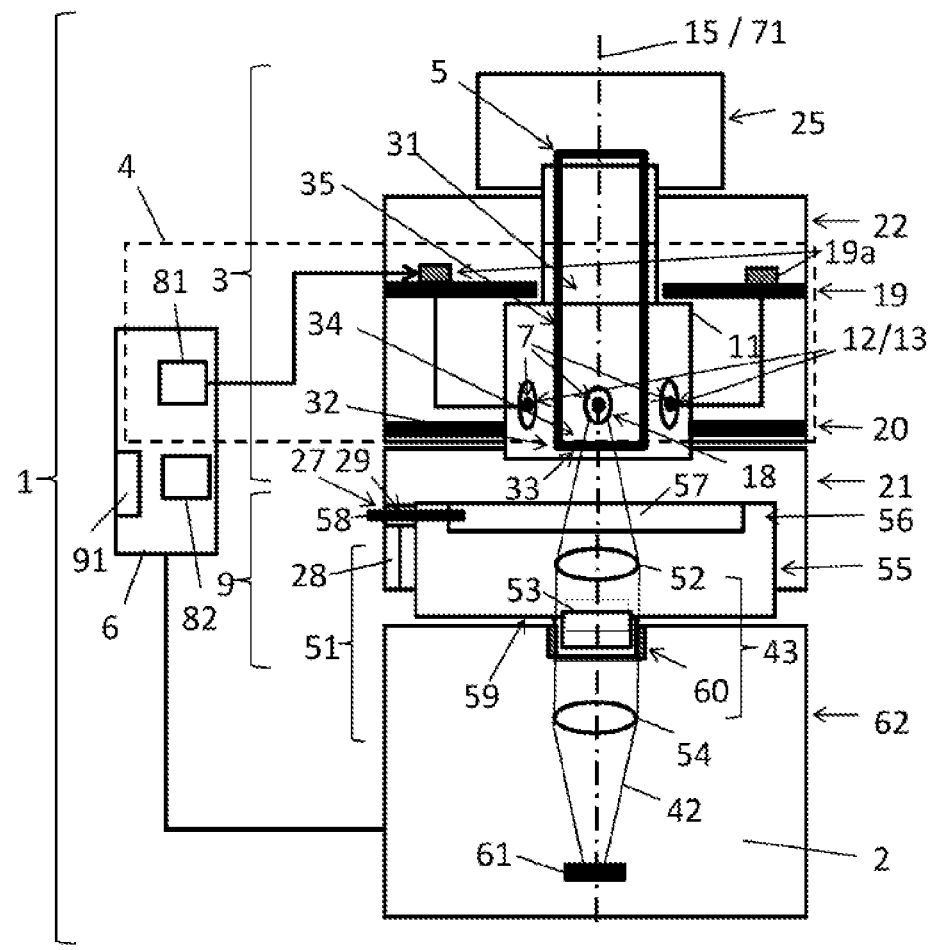
FIG. 1 shows a schematic illustration of a measuring device.
Figure 1:
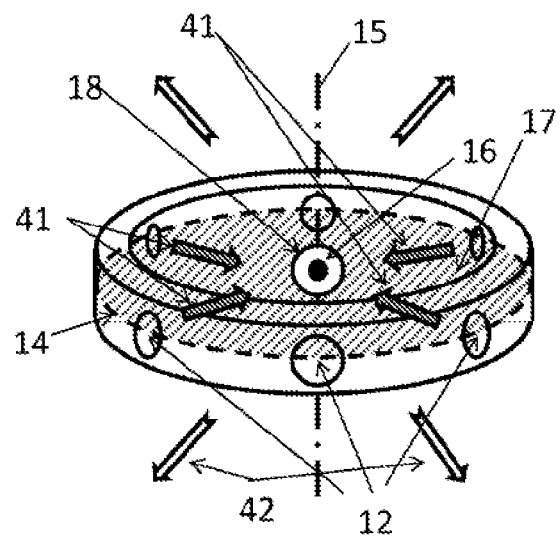

FIG. 1 schematically illustrates a measuring device 1. The latter comprises a photosensitive detector 2, an optical module 9 arranged thereabove, and an excitation module 3 of an excitation source 4. The excitation module 3 is simultaneously designed as a cuvette mount for a cuvette 5. Furthermore, a control and evaluation unit 6 is provided, which acquires and evaluates measurement results of the photosensitive detector 2 and at the same time brings about driving of illuminants 7 of the excitation module 3 or of the excitation source 4. In the embodiment illustrated, therefore, a component part of the excitation source 4 is a part of the control and evaluation unit 6 component part of the light source 4.

In the embodiment illustrated, the excitation module 3 comprises an illuminant holder 11, on or in which a plurality of illuminants 7, preferably designed as light-emitting diodes, are arranged. Hole openings of holes 12 in the illuminant holder 11, which is formed for example from metal, particularly preferably from high-grade steel, represent emission positions 13 for excitation light 41.

The holes 12 are arranged on a circle 14 preferably equidistantly relative to one another (cf. schematic perspective illustration of excerpt in FIG. 1). The illuminant holder 11 is preferably designed to be rotationally symmetrical with respect to an axis 15. Said axis 15 likewise runs through the midpoint 16 of a circle plane 17 of the circle 14, said plane being illustrated in a hatched manner for clarification. Illuminants 7 arranged in the holes 12 and designed as light emitting diodes therefore emit the excitation light 41 from different directions onto the midpoint 16 of the circle 14. It is thus expedient to define a measurement volume 18 such that the latter encloses the midpoint 16 of the circle 14.

In the embodiment illustrated, a portion 19a of the driving electronics for the illuminants 7, i.e. the light emitting diodes, is arranged on a driver circuit board 19, which belongs to the excitation module 3 and is fixed to the illuminant holder 11. In the embodiment illustrated, the individual illuminants are preferably fixed to an illuminant circuit board 20, which, for its part, is fixed on an excitation module carrier 21, on which the illuminant holder 11 is also arranged. The excitation module 3 is enclosed by an excitation module cover 22, which preferably in the same way as the illuminant holder 11 and the excitation module carrier 21 are formed from metal, preferably high-grade steel. The excitation module cover 22 has an opening, through which a cuvette 5 can be introduced into the excitation module. Said cuvette 5 is preferably produced from a cylindrical transparent material, for example quartz glass. A cavity 31 is formed in such a way that it encloses the measurement volume 18.

In order to prevent stray light from penetrating into the cuvette 5, the latter is covered with a cuvette cover 25. The cuvette cover 25 is preferably likewise produced from metal, particularly preferably from high-grade steel.

A base 32 of the cuvette 5 is preferably planar and optically polished. An inner side 34 of the base 32 is preferably likewise planar and optically polished. The outer side 33 and the inner side 34 are preferably oriented plane-parallel and perpendicularly to the optical axis 71 linking the measurement volume 18 to the detector 2. Flame polishing generally suffices in the case of the cuvette wall 35. In principle, the surface constitution is more important at the outer surfaces since here the jump in refractive index relative to air that occurs is greater than that occurring at the inner side relative to a liquid.

The excitation light 41 emitted from the different emission positions 13 excites photosensitizers in the cuvette 31, which thereupon undergo transition to an excited state and in part undergo transition to the triplet state. By way of an impact reaction with triplet oxygen, oxygen is converted to the singlet state. The majority of the singlet oxygen is converted to the triplet ground state via non-radiative transitions or reacts with other constituents. Only a fraction of the singlet oxygen atoms undergoes transition to the triplet oxygen ground state with emission of a luminescence photon, i.e. with emission of luminescence light 42.

A portion of the luminescence light 42 which emerges through the base 32 of the cuvette 5 and enters into the optical module 9 is imaged onto the photosensitive detector 2. The optical module 9 comprises an imaging optical unit 51 comprising a first converging lens 52. The measurement volume 18 imaged on the detector is defined by the imaging optical unit 51. Particular preference is given to imagings or configurations of the imaging optical unit in which an area of the measurement volume parallel to a detection area 61, which constitutes the active area of the detector, has the same size as this active detection area 61. The imaging optical unit 51 overall ideally performs a 1:1 imaging. In such an embodiment, the measurement volume 18 is situated at the distance of the focal length of the first converging lens 52 upstream thereof. Said first converging lens 52 parallelizes the luminescence light 42 originating from the measurement volume 18 in a region 43 below the first converging lens 52, i.e. downstream thereof in the passage direction. A bandpass filter 53 is arranged in this region 43 of parallel beam guiding. Said bandpass filter is preferably designed as an interference filter. A second converging lens 54 is arranged between the bandpass filter 53 and the detection area 61 and images the parallelized and bandpass-filtered luminescence light 42 originating from the measurement volume onto the active detection area 61 of the photosensitive detector 2. The second converging lens 54 ends the region 43 of parallel beam guiding in the direction of propagation of the luminescence light 41. The second converging lens 54 can be integrated into the photosensitive detector.

In an alternative embodiment, the bandpass filter 53 is designed as a variably adjustable bandpass filter and can be tilted by means of a stepper motor relative to an optical axis 71, to which the luminescence light 41 is oriented parallel between the first converging lens 52 and the second converging lens 54. An average wavelength of the bandpass which can pass through the filter is varied by this means. Yet another embodiment provides for using a variable filter comprising electrically drivable liquid crystal components.

An optical module cover and mount 55 is likewise produced in a manner opaque to light, preferably from a metal, particularly preferably from high-grade steel. By way of example, an external thread 60 can be arranged at a lower end 59 of the optical module cover and mount 55, said external thread being screwed to a housing 62 of the photosensitive detector 2.

An adjustable iris diaphragm 57 is arranged at an upper end 56 of the optical module 9 facing the cuvette 5. An adjusting lever 58 projects radially away from the optical axis 71 toward the outside.

The excitation module 3 and the optical module 9 can be screwed together or just plugged onto one another. By means of a vertical alignment in which the optical axis 71 and likewise the axis 15 are aligned parallel to the gravitational force, the gravitational force can be utilized for fixing the individual modules or else only individual instances of the modules onto one another. In one preferred embodiment, such as that illustrated in FIG. 1, the illumination carrier 21 is provided with an L-shaped groove 27, into the short leg 28 of which the adjusting lever 58 of the iris diaphragm engages when the latter is in a closed state, i.e. permits no transmission of light. In addition to the groove 27, the excitation module 3 and the optical module 9 preferably have further guide means, for example projections and depressions, which enable a positioning of the excitation module 3 on the optical module 9 in only a few rotational positions, preferably only a single rotational position, with respect to the optical axis 71 or the axis 15. If the iris diaphragm 57 is then opened by the adjusting lever 58 being rotated with respect to the optical axis 71, said adjusting lever 58 slides into the long leg 29 of the groove 27, which is of L-shaped design, and interlocks the excitation module 3 with the optical module 9 in a positively locking manner. This ensures that the excitation module 3 cannot be removed from the optical module 9 as long as the iris diaphragm is open. Damage to the photosensitive detector 2 can thereby be avoided.

Figure 2:
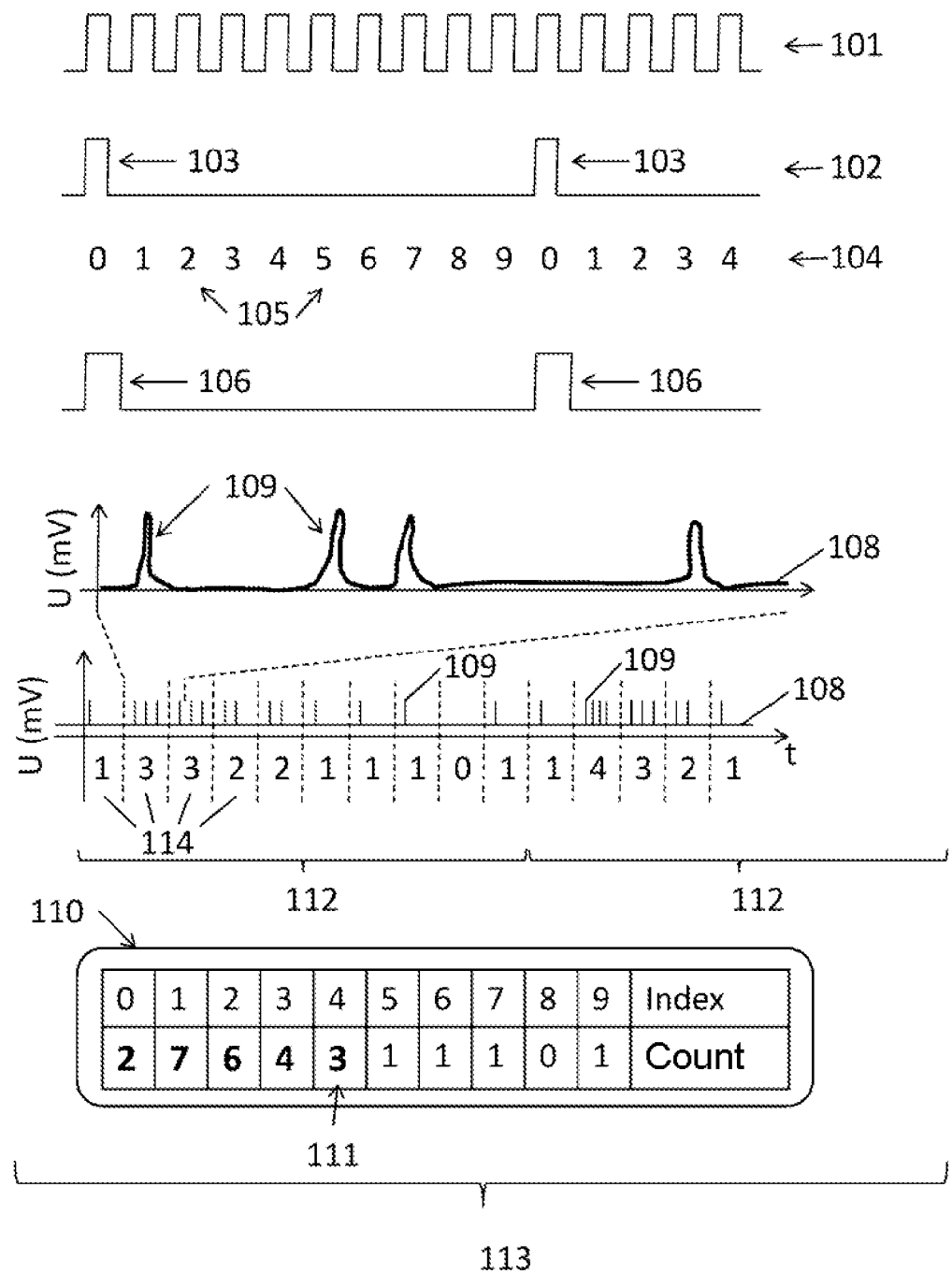
FIG. 2 shows a schematic illustration for illustrating a measurement sequence.

The control and evaluation unit 6 has the driving electronics 81, which, if appropriate with the electronic circuit arranged on the driver circuit board 19 and the illuminant arranged on the illuminant circuit board 20, bring about a pulsed light excitation. A typical pulse duration of the excitation is 100 ns, for example, and the ratio between excitation duration and subsequent measurement time is chosen to be 1:1000, for example. For such a time voltage of 100 ns, for example light emitting diodes having a housing diameter of 5 mm and a design continuous wave current of 20 mA can be energized with 2 A, in order to achieve a high luminous efficiency, without being destroyed. The embodiment of the illuminant holder 11 and of the excitation module cover 22 and of an excitation module carrier 21 from high-grade steel enables a good dissipation of heat from the illuminants 7 to the surroundings. The control and evaluation unit 6 furthermore comprises evaluation means 82, implemented for example in a field programmable gate array. The measurement and evaluation in the temporal sequence will be illustrated schematically with reference to FIG. 2.

A quartz oscillator generates an oscillation signal 101, which supplies a time base. A start pulse signal 102 is generated in a manner derived therefrom, said start pulse signal comprising start pulses 103 preferably in equidistant time segments. The start pulse 103 starts an index counter 104, for example, which counts continuously upward or downward in equidistant time steps derived from the oscillation signal 101 and assumes index counter values 105. Furthermore, the start pulse 103 activates the excitation source, which emits excitation light into the measurement volume for an excitation pulse duration 106. The photosensitive detector receives a detection signal 108 comprising individual event pulses 109. An excerpt from the detection signal 108 is illustrated in an enlarged manner. Otherwise the detection signal 108 is illustrated in a schematically stylized manner. The number of events detected in the individual time segments 114 is indicated below the schematically stylized detection signal 108. Incremental counters 111 are realized in a memory area 110 addressable via the index counter 104 or the index counter values 105. Whenever an event pulse 109 is detected, the incremental counter 111 in the memory area 110 which is addressed by the current index counter value 105 is incremented, or decremented in other embodiments. As soon as a new start pulse 103 occurs, the counter is started anew and an excitation light pulse is emitted again. A plurality of such excitation cycles 112 are combined to form a measurement cycle 113, at the end of which the incremental counters 111, i.e. the memory values of the memory area 110, are read and output for example via an interface 91 (see FIG. 1), in particular a USB interface or RS232 interface. In the example illustrated, the counter values of the incremental counters 0 to 4 are in each case printed in bold in order to indicate that the detected events of the second excitation cycle have already been acquired. This has not yet taken place in the incremental counters 5 to 9. The index counters are thus shown at the point in time at which the representation of the second excitation cycle 112 terminates.

Figure 3:
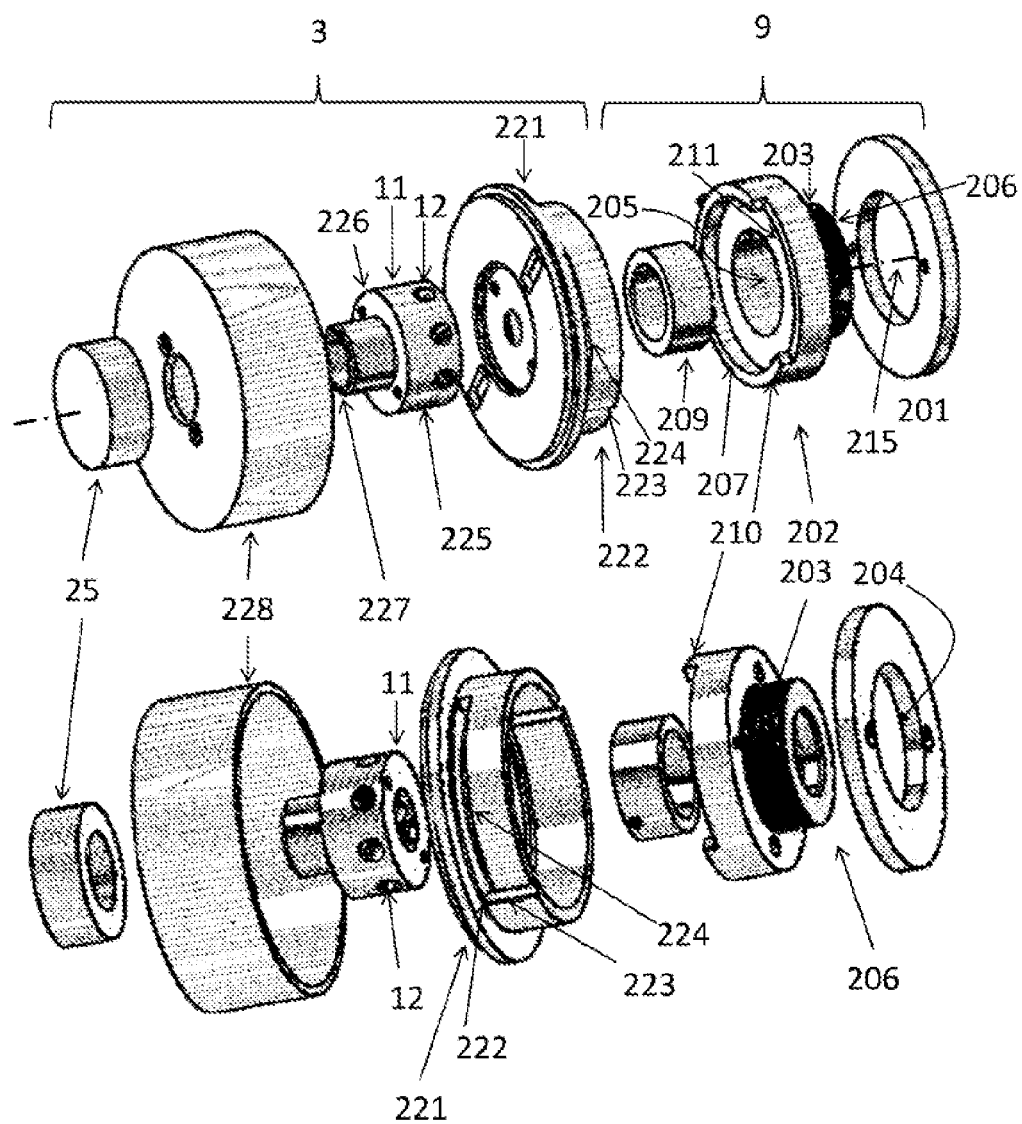
FIG. 3 shows a schematic exploded drawing of components of an optical module and of an excitation module.

FIG. 3 shows a schematic exploded drawing of the components of the optical module 9 and of an excitation module 3, said components being produced from high-grade steel, for example. Two different perspective views of the same modules are illustrated. The optical module 9 comprises a baseplate 201, which is screwed to an optical system mount 202. The optical system mount 202 has an external thread 203 at a lower end, which external thread, in the screwed state with the baseplate 201, projects through an opening 204 in the baseplate 201 in order to be screwed into a housing of a photosensitive detector, for example of a photomultiplier. The optical system mount 202 has a through-opening 205, which, at an end 206 facing the external thread, is tapered by a flange projecting into the through-opening 205. An interference filter can be placed onto this, said interference filter being introduced into the through-opening 205 from the opposite end 207 facing away from the end 206. Furthermore, a lens mount 209 is introduced into the optical system mount 202, the first converging lens being mounted in said lens mount. Between the lens holder 209 and the flange formed at the end 206, the filter (not illustrated) is clamped in the optical system mount 202.

The optical system mount 202 furthermore has an axially projecting wall 210 at the opposite end 207, a circle sector element 211 being cut out from said wall. The adjusting lever of the iris diaphragm (neither being illustrated) is received in the region of said circle sector element 211, said iris diaphragm being introduced into the opposite end 207 above the lens holder 209. In one preferred embodiment, the second lens of the imaging optical unit is already integrated into the housing of the photosensitive detector, for example of a photosensitive detector from Hamamatsu. The iris diaphragm (not illustrated) terminates the optical unit.

An excitation module carrier 221 is arranged on the optical module 9. Said carrier is designed such that it can be placed onto the optical module or the optical system mount preferably only in one rotational orientation with respect to an axis 215 of symmetry, which coincides with the optical axis 71 according to FIG. 1. The carrier additionally comprises an L-shaped groove 222, into which the lever of the iris diaphragm engages upon placement in the closed state of the iris diaphragm. In this case, the lever moves into a short leg 223 of the L-shaped groove 222. If the excitation module carrier 221 has been placed onto the optical module 9 or the optical system mount 202 and if the iris diaphragm is open, then the adjusting lever thereof engages into the long leg 224 of the L-shaped groove 222 and produces a positively locking connection between the optical system mount 202 and the excitation module carrier 221.

On the excitation module carrier 221, an illuminant circuit board (not illustrated) is fixed together with an illuminant holder 11, which is simultaneously designed as a cuvette holder. The illuminants 7 designed as light emitting diodes are arranged in the holes 12 in the illuminant holder 11 (cf. FIG. 1). The diameter 225 of the illuminant holder 11 tapers above an arrangement position of the holes 12, such that a driver circuit board can be applied on a shoulder 226, said driver circuit board having a circular hole for receiving an upper shaft 227 of the illuminant holder 11. To protect against stray light, an excitation module cover 22 is fixed above the illuminant holder 11 on the excitation module carrier. Through an opening in the excitation module cover 228 it is possible to introduce cuvettes into the illuminant holder 11, which are moved in in a gravity-driven manner, provided that the axis 215 of symmetry is aligned perpendicularly. A cuvette cover 25 brings about the complete encapsulation of the measurement volume and of the imaging path to the photosensitive detector against stray light.

In order to be able to carry out excitation at different wavelengths, it is advantageous to provide a plurality of excitation or illumination modules each having different illuminants. If the illumination modules or excitation modules 3 are only plugged onto the optical module 9, then rapid and simple exchange of the excitation modules is possible. Even in the case of a screw connection, only a small number of screws have to be provided with holes and fixed again. A very flexible measuring device is provided in any case.

In a differently embodied embodiment, the various emission positions can be ends of optical fibers which for example can alternatively be introduced into the holes 12 in the illuminant holder. However, such an embodiment is mechanically very much more complex and less compact. A particular advantage in the use of light emitting diodes as excitation light source is that there is no need for specially trained personnel, who are necessary for example when lasers are used as excitation light sources. A high light intensity can nevertheless be achieved in order to perform reliable and rapid measurements.

Figure 4:
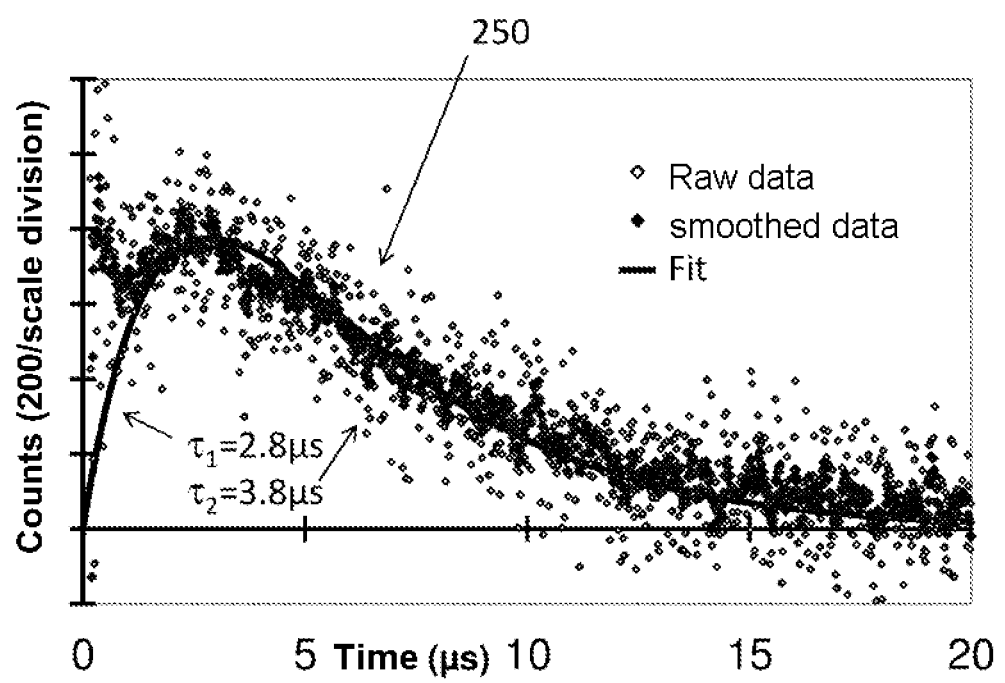
FIG. 4 shows a schematic illustration of a measurement result.

This is illustrated in FIG. 4, for example, which illustrates a measurement result for a measurement of the singlet oxygen luminescence of a humic substance in water. Such a measurement is currently possible only for a few selected specialists globally with significantly more complex equipment. The total measurement time for obtaining the result illustrated was 100 s. Before curve fitting, the raw data were subjected to smoothing. It can readily be discerned on the basis of the measurement curve 250 that firstly a rise in the singlet oxygen luminescence via formation of the singlet oxygen from the photosensitizers takes place and then a reaction or a non-radiative decomposition in parallel with the luminescence decomposition takes place, which leads to the decay of the luminescence signal. It is expressly pointed out at this juncture that the decay time period and time constant are not dominated by the life time of the radiation transition, but rather exclusively by other processes.

Figure 5:
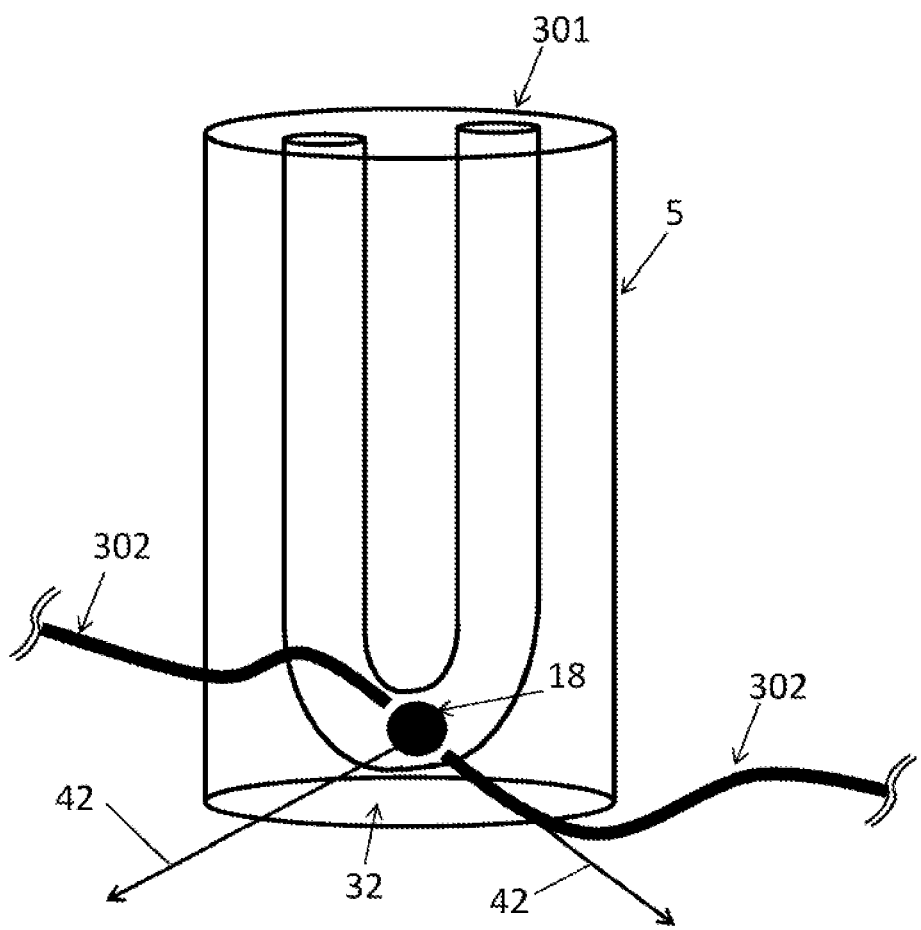
FIG. 5 shows a schematic illustration of a cuvette.

FIG. 5 shows a further alternative embodiment of a cuvette, comprising a U-shaped tube 301. Flow can thereby take place through the measurement volume, such that, during repeated measurement cycles, measurement solution not irradiated previously is used in each case. A possible influence on the measurement by reaction products that were produced in a preceding measurement cycle can thereby be reduced. The cuvette is of cylindrical design and adapted such that it can be introduced into the illuminant holder of a measuring device, said illuminant holder being designed as a cuvette holder. Furthermore, an embodiment is illustrated here in which the excitation light is radiated in via optical fibers 302. In this design, too, in which the U-shaped tube can also have a square or rectangular cross section and the section in which the measurement volume 18 lies can have boundary areas parallel to the base 32, luminescence radiation 42 from a large angular range can be imaged onto the detector. Above the U-shaped arc, a reflector, for example a mirror, which increases a luminescence radiation efficiency, can be integrated into the cuvette.

Figure 6:
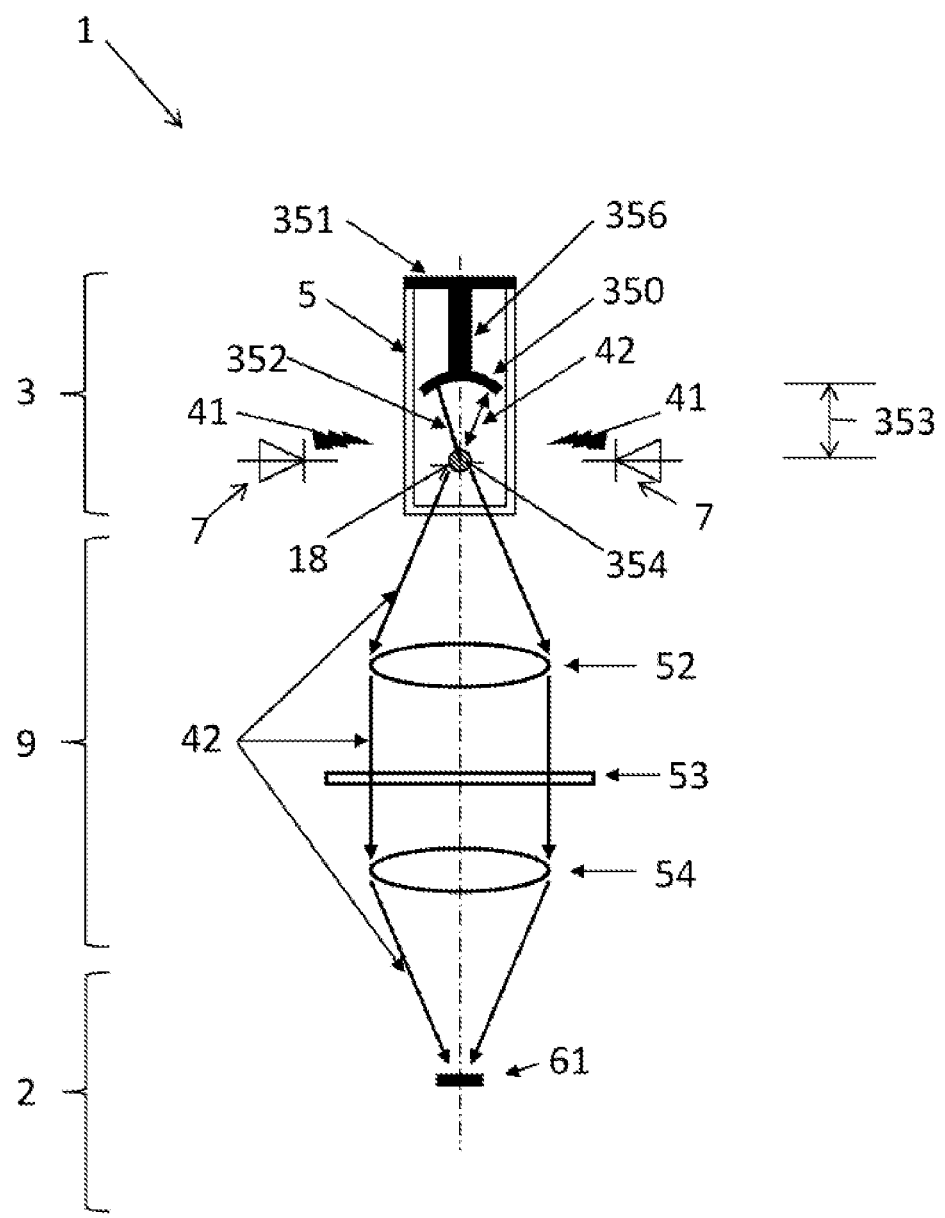
FIG. 6 shows a further schematic illustration of beam guiding with the use of an additional reflector.

FIG. 6 schematically shows the construction of further embodiments of a measuring device 1 and the beam guiding of the luminescence radiation 42. Only the essential components of the detector 2, the optical module 9 and the excitation module 3 are shown. The optically active detection area 61 of the detector 2 is illustrated. The luminescence radiation 42 of the measurement volume 18 is imaged onto said optically active detection area 61 via the first converging lens 52 and the second converging lens 54. The imaging takes place substantially along the optical axis 71 linking the active detection area 61 to the measurement volume 18.

Between the first converging lens 52 and the second converting lens 54, the beam guiding paths of the luminescence radiation 42 run parallel. The bandpass filter 53 is arranged in this region, and transmits only the wavelength of the radiation transition of singlet oxygen to triplet oxygen. Alternatively, it is possible to use a variable bandpass filter comprising liquid crystal components, for example, which are driven electrically.

This embodiment does not comprise an iris diaphragm since the latter principally serves for protecting the detector 2, when the excitation module 3 is changed. Other embodiments can provide an iris diaphragm that can be arranged at any desired location in the optical module 9 upstream of the detector 2.

In the embodiment illustrated, only two light emitting diodes of the excitation module are schematically illustrated as illuminants 7 which emit excitation light 41.

A preferably spherical mirror 350 on a mirror mount 351 is suspended into the cuvette 5. A radius 352 of curvature of the preferably spherical mirror 350 and a distance 353 from a center 354 of the measurement volume 18 are coordinated with one another such that they correspond to one another. Consequently, luminescence light 42 which originates from the measurement volume 18 and which impinges on the preferably spherical mirror 350 is reflected again into the measurement volume 18. The yield of luminescence photons can thereby be increased by up to a factor of 2 (disregarding reflection and absorption losses).

The mirror 350 has a high reflectivity, preferably a maximum, at the wavelength of the luminescence light from the singlet oxygen. The mirror can be wholly or partly dipped into the solution or the substrate in which the measurement is performed. In other configurations, the mirror can be integrated into the cuvette.

For optimum adjustment of the distance 353, the mirror mount 351 can comprise an adjusting device 356, which can be designed for example as a set screw (not illustrated).

It is obvious to a person skilled in the art that only exemplary embodiments are illustrated and the individual features described in the various embodiments and for the various embodiments can be used in any desired combination for realizing the invention.

LIST OF REFERENCE SIGNS

1 Device
2 Photosensitive detector
3 Excitation module
4 Light source
5 Cuvette
6 Control and evaluation unit
7 Illuminant
9 Optical module
11 Illuminant holder
12 Holes
13 Emission position
14 Circle
15 Axis
16 Midpoint
17 Circle plane
18 Measurement volume
19 Driver circuit board
19a Portion of the driving electronics
20 Illuminant circuit board
21 Excitation module carrier
22 Excitation module cover
25 Cuvette cover
27 Groove
28 Short leg
29 Long leg
31 Cavity
32 Base
33 Outer side
34 Inner side
35 Cuvette wall
41 Excitation light
42 Luminescence light
43 Region (of parallel beam guiding)
51 Imaging module
52 First converging lens
53 Bandpass filter
54 Second converging lens
55 Optical module cover and mount
56 Upper end
57 Iris diaphragm
58 Adjusting lever
59 Lower end
60 External thread
61 (Active) detection area
62 Housing
71 Optical axis
81 Driving electronics
82 Evaluation means
91 Interface
101 Oscillation signal
102 Start pulse signal
103 Start pulses
104 Index counter
105 Index counter values
106 Excitation pulse duration
108 Detection signal
109 Measurement pulses
110 Memory area
111 Incremental counter
112 Excitation cycle
113 Measurement cycle
114 Time segment
201 Baseplate
202 Optical system mount
203 External thread
204 Opening
205 Through-opening
206 End
207 Opposite end
208 Lens holder
210 Wall
211 Circle sector element
215 Axis of symmetry
221 Excitation module carrier
222 L-groove
223 Short leg
224 Long leg
225 Diameter
226 Shoulder
227 Upper shaft
250 Measurement curve
301 U-shaped tube
302 Optical fibers
350 Spherical mirror
351 Mirror mount
352 Radius of curvature
353 Distance
354 Center
356 Adjusting device

The invention claimed is:

1. A measuring device for measuring singlet oxygen luminescence being excited by at least one photosensitizer, the measuring device comprising:
a photosensitive detector;
an excitation source configured for radiating excitation light from a plurality of emission positions into a measurement volume for exciting the at least one photosensitizer, said excitation source containing at least one light emitting diode directly generating the excitation light for exciting the at least one photosensitizer in the measurement volume; and
a control and evaluation unit coupled to said photosensitive detector and said excitation source;
wherein the measuring device is embodied such that ambient light from outside cannot be incident on the photosensitive detector or on the measurement volume;
wherein the measurement volume and said photosensitive detector are aligned along a vertical axis, said measurement volume is disposed above said photosensitive detector; and
further comprising an optical module disposed between the measurement volume and said photosensitive detector, said optical module having an imaging optical unit imaging at least part of luminescence radiation generated in the measurement volume onto an active area of said photosensitive detector;

wherein said excitation source contains at least one exchangeable excitation module which can be placed onto said optical module; and wherein:

said optical module contains an adjustable iris diaphragm with an adjusting lever; and said excitation module has an excitation module carrier with a groove formed therein and into said groove said adjusting lever of said iris diaphragm engages in a course of said excitation module being disposed on said optical module, said groove shaped such that said adjusting lever of said iris diaphragm of said optical module connects to said excitation module in a form-locking manner when said iris diaphragm is open, and separation of said excitation module and said optical module is possible only in a closed position of said iris diaphragm.

2. The measuring device according to claim 1, wherein at least a large number of said emission positions are disposed on a circle, the circle is disposed with respect to the measurement volume such that a midpoint of the circle is enclosed by the measurement volume or an axis oriented perpendicularly to a circle plane and running through the midpoint of the circle pierces the measurement volume.

3. The measuring device according to claim 1, wherein said light emitting diode is one of a plurality of light emitting diodes disposed at the emission positions.

4. The measuring device according to claim 1, further comprising optical fibers ending at the emission positions.

5. The measuring device according to claim 1, wherein said optical module has a bandpass filter being adjustable in a variable manner.

6. The measuring device according to claim 1, further comprising: a cuvette having a hollow volume; wherein said excitation source is a cuvette mount, such that said cuvette introduced into said cuvette mount remains in a gravity-driven manner in the measurement position in which said hollow volume of said cuvette encloses the measurement volume.

7. A measuring device for measuring singlet oxygen luminescence being excited by at least one photosensitizer, the measuring device comprising:

a photosensitive detector;

an excitation source configured for radiating excitation light from a plurality of emission positions into a measurement volume for exciting the at least one photosensitizer, said excitation source containing at least one light emitting diode directly generating the excitation light for exciting the at least one photosensitizer in the measurement volume; and a control and evaluation unit coupled to said photosensitive detector and said excitation source;

wherein the measuring device is embodied such that ambient light from outside cannot be incident on the photosensitive detector or on the measurement volume; and further comprising a mirror disposed at a side of the measurement volume facing away from said photosensitive detector, said mirror reflecting luminescence light at least one of into the measurement volume or onto said photosensitive detector.

8. The measuring device according to claim 7, wherein at least a large number of said emission positions are disposed on a circle, the circle is disposed with respect to the measurement volume such that a midpoint of the circle is enclosed by the measurement volume or an axis oriented perpendicularly to a circle plane and running through the midpoint of the circle pierces the measurement volume.

9. The measuring device according to claim 7, wherein said light emitting diode is one of a plurality of light emitting diodes disposed at the emission positions.

10. The measuring device according to claim 7, further comprising optical fibers ending at the emission positions.

11. A method for measuring singlet oxygen luminescence, which comprises the steps of:

exciting at least one photosensitizer by excitation light from an excitation source;

detecting a luminescence light of the singlet oxygen luminescence via a photosensitive detector;

evaluating the luminescence light detected via a control and evaluation unit coupled to the photosensitive detector and the excitation source;

controlling the exciting of the singlet oxygen luminescence, the detecting of the luminescence light of the singlet oxygen luminescence and the evaluating of the luminescence light by means of the control and evaluation unit; and when performing the step of exciting the at least one photosensitizer, radiating the excitation light from the excitation source from a plurality of emission positions into a measurement volume for exciting the at least one photosensitizer and the excitation source containing at least one light emitting diode and light from the at least one light emitting diode is radiated directly as the excitation light for the at least one photosensitizer into the measurement volume;

wherein ambient light from outside cannot be incident on the photosensitive detector or on the measurement volume and wherein further a mirror is disposed at a side of the measurement volume facing away from said photosensitive detector, said mirror reflecting luminescence light onto said photosensitive detector.

* * * * *